(12) United States Patent
Parto et al.

(10) Patent No.: US 10,022,187 B2
(45) Date of Patent: Jul. 17, 2018

(54) FORWARD SCANNING-OPTICAL PROBES, CIRCULAR SCAN PATTERNS, OFFSET FIBERS

(71) Applicant: Novartis AG, Basel (CH)

(72) Inventors: Kambiz Parto, Laguna Niguel, CA (US); Barry Wheatley, Oceanside, CA (US); Edouard Schmidtlin, Studio City, CA (US); Tammo Heeren, Aliso Viejo, CA (US); Mauricio Jochinsen, Fountain Valley, CA (US); Lingfeng Yu, Lake Forest, CA (US)

(73) Assignee: Novartis AG, Basel (CH)

( * ) Notice: Subject to any disclaimer, the term of this patent is extended or adjusted under 35 U.S.C. 154(b) by 275 days.

(21) Appl. No.: 14/134,668

(22) Filed: Dec. 19, 2013

(65) Prior Publication Data

US 2015/0173622 A1 Jun. 25, 2015

(51) Int. Cl.
*A61B 18/20* (2006.01)
*A61B 18/22* (2006.01)
(Continued)

(52) U.S. Cl.
CPC ............ *A61B 18/20* (2013.01); *A61B 5/0066* (2013.01); *A61B 18/22* (2013.01); *A61B 5/0084* (2013.01);
(Continued)

(58) Field of Classification Search
CPC ... A61B 5/0066; A61B 5/0084; A61B 5/0059; A61B 18/20
(Continued)

(56) References Cited

U.S. PATENT DOCUMENTS 5,595,565 A  1/1997  Treat et al.
6,004,314 A  12/1999  Wei et al.
(Continued)

FOREIGN PATENT DOCUMENTS

DE  102008036420  11/2010
EP  2832543 A1  2/2015
(Continued)

OTHER PUBLICATIONS

Merriam-Webster Dictionary ("cannula" definition, http://www.merriam-webster.com/dictionary/cannula).*
(Continued)

*Primary Examiner* — Carolyn Pehlke
(74) *Attorney, Agent, or Firm* — S. Brannon Latimer (57) ABSTRACT

An optical light scanning probe is presented, the probe comprising a handle, shaped for grasping by a user; a cannula, protruding from a distal portion of the handle with an outer diameter smaller than 20 gauge; an optical fiber with a distal fiber-portion off a probe-axis, configured to receive a light from a light-source at a proximal fiber-portion, and to emit the received light at the distal fiber-portion; a fixed beam forming unit, disposed at a distal portion of the cannula, configured to receive the light from the distal fiber-portion, and to deflect the received light toward a target region; and a fiber actuator, housed at least partially in the handle, configured to move the distal fiber-portion to scan the deflected light along a scanning curve in the target region.

18 Claims, 6 Drawing Sheets

(51) Int. Cl.
*A61B 5/00* (2006.01)
*A61B 18/00* (2006.01)

(52) U.S. Cl.
CPC ... *A61B 18/201* (2013.01); *A61B 2018/00577* (2013.01); *A61B 2018/00589* (2013.01); *A61B 2018/00982* (2013.01); *A61B 2018/20357* (2017.05); *A61B 2560/0431* (2013.01)

(58) Field of Classification Search
USPC .................. 600/425, 433–435, 476, 478
See application file for complete search history.

(56) References Cited

U.S. PATENT DOCUMENTS

| | | |
|---|---|---|
| 6,485,413 B1 | 11/2002 | Boppart et al. |
| 6,564,087 B1 | 5/2003 | Pitris et al. |
| 7,261,687 B2 | 8/2007 | Yang |
| 7,364,543 B2 | 4/2008 | Yang et al. |
| 7,602,540 B2 | 10/2009 | Masuda et al. |
| 8,325,988 B2 | 12/2012 | Ren et al. |
| 8,602,975 B2 | 12/2013 | Ohzawa |
| 2003/0004412 A1* | 1/2003 | Izatt .................. A61B 5/0066 600/425 |
| 2005/0020926 A1 | 1/2005 | Wiklof et al. |
| 2005/0234345 A1 | 10/2005 | Yang |
| 2006/0004397 A1 | 1/2006 | Osawa |
| 2007/0016062 A1 | 1/2007 | Park et al. |
| 2007/0066871 A1 | 3/2007 | Yang et al. |
| 2007/0265602 A1 | 11/2007 | Mordaunt et al. |
| 2008/0051770 A1 | 2/2008 | Scheller et al. |
| 2008/0285909 A1* | 11/2008 | Younge ............... A61B 5/1076 385/13 |
| 2009/0015894 A1 | 1/2009 | Rosman et al. |
| 2009/0198125 A1 | 8/2009 | Nakabayashi et al. |
| 2010/0228119 A1 | 9/2010 | Brennan et al. |
| 2010/0228123 A1 | 9/2010 | Brennnan et al. |
| 2010/0228124 A1 | 9/2010 | Brennan et al. |
| 2010/0228132 A1 | 9/2010 | Brennan et al. |
| 2010/0228238 A1 | 9/2010 | Brennan et al. |
| 2011/0184390 A1 | 7/2011 | Zanni et al. |
| 2011/0279821 A1 | 11/2011 | Brennan et al. |
| 2011/0282190 A1 | 11/2011 | Caffey et al. |
| 2011/0282191 A1 | 11/2011 | Brennan et al. |
| 2011/0282331 A1 | 11/2011 | Brennan et al. |
| 2012/0075639 A1 | 3/2012 | Brennan et al. |
| 2012/0190921 A1 | 7/2012 | Yadlowsky et al. |
| 2012/0245569 A1 | 9/2012 | Papac et al. |
| 2012/0310042 A1* | 12/2012 | Joos .................. A61B 18/20 600/108 |
| 2013/0038836 A1 | 2/2013 | Smith |
| 2013/0058533 A1 | 3/2013 | Ren et al. |
| 2013/0144278 A1 | 6/2013 | Papac et al. |
| 2013/0150839 A1 | 6/2013 | Smith et al. |
| 2013/0158392 A1 | 6/2013 | Papac et al. |
| 2013/0158393 A1 | 6/2013 | Papac et al. |
| 2013/0267776 A1 | 10/2013 | Brennan et al. |
| 2014/0327947 A1 | 11/2014 | Lin et al. |

FOREIGN PATENT DOCUMENTS

| | | |
|---|---|---|
| GB | 2222953 | 3/1990 |
| JP | 2008-539887 A | 11/2008 |
| JP | 2013-092779 A | 5/2013 |
| JP | 2013-220171 A | 10/2013 |
| WO | 2007/038682 | 4/2007 |
| WO | 2008/079526 | 7/2008 |
| WO | 2010/047190 A1 | 4/2010 |
| WO | 2012/100138 | 7/2012 |
| WO | 2013/146259 A1 | 10/2013 |

OTHER PUBLICATIONS

International Search Report and Written Opinion issued for PCT/US2014/068912, dated Mar. 4, 2015, 11 pgs.

Han et al., "Handheld forward-imaging needle endoscope for ophthalmic optical coherence tomography inspection", Journal of Biomedical Optics, Mar./Apr. 2008, vol. 13(2), pp. 020505-1 thru 020505-3.

Tearney GJ et al., "Scanning single-mode fiber optic catheter-endoscope for optical coherence tomography", Optics Letters, Apr. 1, 1996, vol. 21(7), pp. 543-545.

Wu et al., "Paired-angle-rotation scanning optical coherence tomography forward-imaging probe", Optics Letters, May 2006, vol. 31(9), 1265-1267.

Xie, T., "Fiber-optic-bundle-based optical coherence tomography", Opt. Lett. 30, 2005, pp. 1803-1805.

Yaqoob et al., "Methods and application areas of endoscopic optical coherence tomography", Journal of Biomedical Optics, Nov./Dec. 2006, vol. 11(6), pp. 063001-1 thru 063001-19.

* cited by examiner

FORWARD SCANNING-OPTICAL PROBES, CIRCULAR SCAN PATTERNS, OFFSET FIBERS

BACKGROUND

Technical Field

Embodiments disclosed herein are related to forward scanning optical probes with fiber actuator systems. Embodiments can be used in devices such as Optical Coherence Tomography (OCT) probes, laser coagulation and laser ablation devices.

Related Art

The importance of, and need for, high performance optical probes keeps growing in several fields. They can be used as imaging probes of Optical Coherence Tomography (OCT) systems, in laser coagulation systems and in laser ablation systems.

These probes typically include a handle and a cannula, where the cannula is inserted into a target tissue, such as a human eye. The probes typically also have an optical fiber that carries the light from a light source through the cannula to a distal end of the probe where the light is emitted to a target region of the target tissue. In most existing devices the fiber is affixed to the cannula and thus can image or ablate the spot of the target region to which the cannula is directed to.

Recently, the functionality of some probes has been enhanced by making the fiber capable of moving relative to the cannula. This enhancement can impart a scanning functionality on the probe. For example, such enhanced, or scanning, probes can image or ablate the target region not only at a spot, but along a scanning line. Some scanning probes achieve this scanning functionality by moving an offset moving fiber through a sequence of offset positions. Existing scanning probes are known with the following features.

(1) In some scanning probes, the ultimate distal optical element is fixed to the cannula and the offset fiber is scanning back and forth relative to this optical element along a straight scanning line.

(2) In some scanning probes, the fiber is glued to the ultimate distal optical element, so the fiber and the optical element scan together. Therefore, the ultimate distal optical element is moving relative to the surrounding ophthalmic tissue and the cannula.

(3) In some scanning probes, the actuator that moves the offset fiber is in the disposable portion of the probe.

(4) In some scanning probes, a substantial portion of the actuator is in fact in the cannula itself. This makes a diameter of the cannula larger. Typically, the diameter of these cannulas is larger than 20 gauge.

SUMMARY

Consistent with some embodiments, an optical light scanning probe can comprise a handle, shaped for grasping by a user; a cannula, protruding from a distal portion of the handle with an outer diameter smaller than 20 gauge; an optical fiber with a distal fiber-portion off a probe-axis, configured to receive a light from a light-source at a proximal fiber-portion, and configured to emit the received light at the distal fiber-portion; a fixed beam forming unit, disposed at a distal portion of the cannula, configured to receive the light from the distal fiber-portion, and to deflect the received light toward a target region; and a fiber actuator, housed at least partially in the handle, configured to move the distal fiber-portion to scan the deflected light along a scanning curve in the target region, wherein the probe-axis is one of a cannula-axis and a beam forming unit-axis.

Consistent with some embodiments, an optical imaging system can comprise an Optical Coherence Tomography engine, comprising an imaging light source, and an OCT image detector-processor; and an imaging probe, comprising a handle, and a cannula, protruding from a distal portion of the handle with an outer diameter smaller than 20 gauge; and an optical fiber with a distal fiber-portion off a probe-axis, and configured to guide a light from the imaging light-source; a fixed beam forming unit, disposed at a distal portion of the cannula, configured to deflect the guided light toward a target; and a fiber actuator, housed at least partially in the handle, configured to move the distal fiber-portion to scan the deflected light along a scanning curve in a target region, wherein the probe-axis is one of a cannula-axis and a beam forming unit-axis.

Consistent with some embodiments, a method of imaging with an imaging probe that comprises a handle; a cannula, protruding from the handle with an outer diameter smaller than 20 gauge; an optical fiber with a distal fiber-portion off a probe-axis; and a fixed beam forming unit at a distal portion of the cannula; can comprise receiving a light by the fiber from an imaging light-source at a proximal fiber-portion; emitting the received light by the fiber at the distal fiber-portion towards the fixed beam forming unit; deflecting the emitted light by the fixed beam forming unit; and moving the distal fiber-portion by a fiber-actuator, housed at least partially in the handle of the imaging probe to scan the deflected light along a scanning curve in a target region, wherein the probe-axis is one of a cannula-axis and a beam forming unit-axis.

In the drawings, elements having the same designation have the same or similar functions.

DETAILED DESCRIPTION

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure.

Problems with the above-described features of existing scanning probes include the following.

(1) In scanning probes with the offset fiber scanning back and forth along a straight scanning line, the scanning is not available along curved lines, loops, or circles. Scanning along a circle could allow imaging spherically shaped ophthalmic targets more efficiently. For example, the preparation for a capsulotomy can benefit from imaging the lens capsule along a circle.

(2) In scanning probes with the ultimate distal optical element moving relative to the surrounding ophthalmic tissue, the moving distal optical element can catch pieces of the target tissue which, in turn, can clog the probe and reduce a functionality of the scanning probe itself. Further, the rotation and movement of the distal optical element may cause iatrogenic defects. This is an undesired surgical effect.

(3) The scanning probes with the actuator in the disposable portion of the probe are more expensive as the moving and/or energized actuator, a pricey component, is disposed after each procedure.

(4) The scanning probes with a substantial portion of the actuator in the cannula, are typically forced to have a diameter larger than 20 gauge, likely causing more extensive scar tissue. Also, a larger diameter sclerotomy typically requires suturing, that prolongs healing time and reduces patient comfort.

Embodiments in this patent document offer improvements for at least the above-described problems by applying at least the following designs. (1) Some embodiments may be configured to scan the light beam along a non-linear scanning curve. (2) Some embodiments may have a fixed ultimate distal optical element in the cannula and thus avoid catching pieces of a target tissue. (3) Some embodiments may include a fiber actuator that is largely positioned in the non-disposable portion of the probe or even outside the probe. (4) Some embodiments may include a fiber actuator that is largely positioned outside the cannula, allowing the diameter of the cannula to be smaller than 20 gauge. Some embodiments may contain combinations of the above described designs.

Figure 1:
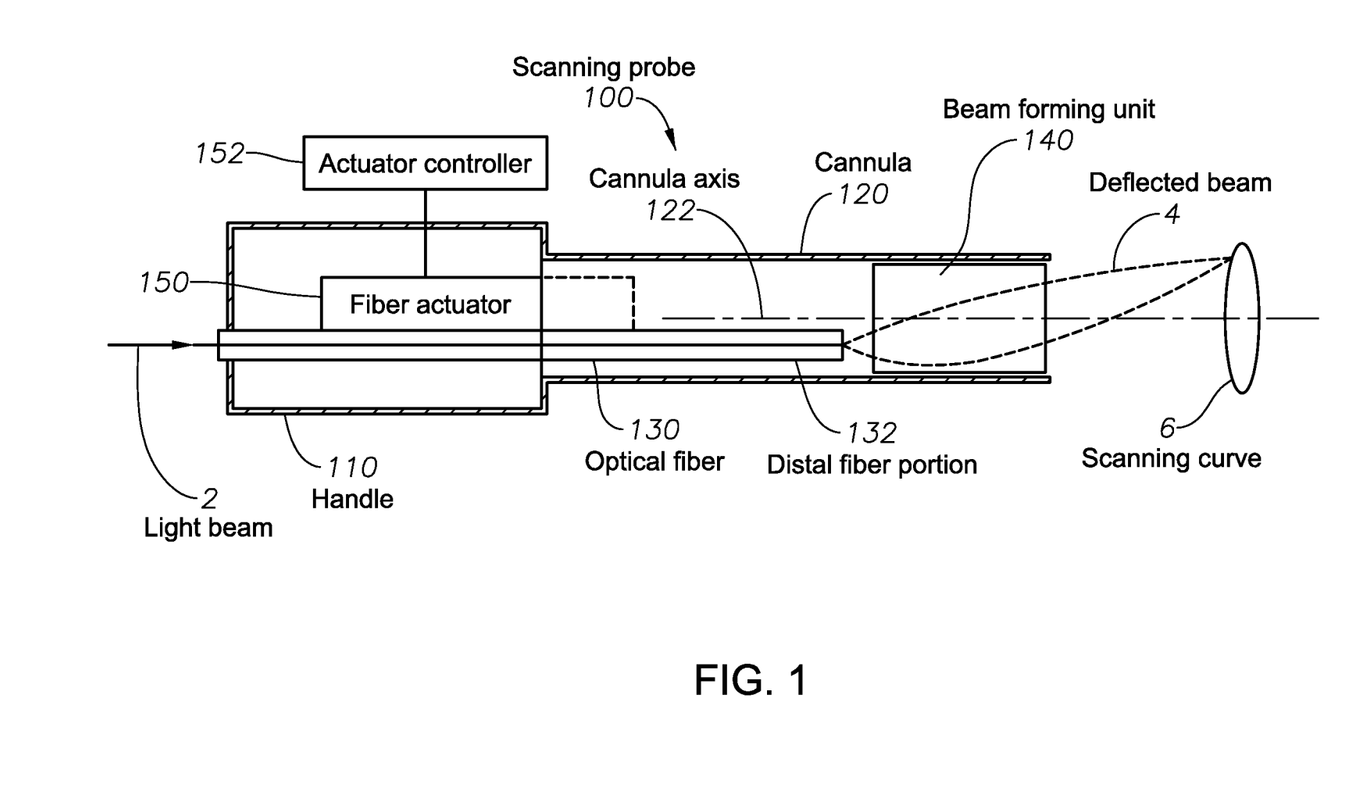
FIG. 1 illustrates an imaging probe.

FIG. 1 schematically illustrates an optical light scanning probe 100 consistent with some embodiments. The scanning probe 100 can include a handle 110, shaped for grasping by a user, a cannula 120, protruding from a distal portion of the handle 110, the cannula 120 having an outer diameter smaller than 20 gauge. The outer diameter of the cannula being less than 20 gauge may address the above outlined problem (4) by reducing the size and amount of scar tissue. The scanning probe 100 can also include an optical fiber 130 with a distal fiber-portion 132 off a cannula-axis 122, wherein the fiber 130 can be configured to receive a light or light beam 2 from a light-source at a proximal fiber-portion, and to emit the received light at the distal fiber-portion 132. In some embodiments, the fiber 130 can be positioned partially in the handle 110, with the distal fiber-portion 132 in the cannula 120.

The scanning probe 100 can also include a fixed beam forming unit 140, disposed at a distal portion of the cannula 120, configured to receive the light beam from the distal fiber-portion 132, and to deflect the received light beam as a deflected light 4 or deflected beam 4 toward a target region. The fixed nature of the beam forming unit 140 may address the above outlined problem (2) by avoiding catching portions of the target tissue in the moving ultimate distal optical element.

In FIG. 1 the distal fiber-portion 132 is shown to be off a cannula-axis 122. In other embodiments, it can be off an axis of the fixed beam forming unit 140. These axes can coincide when the fixed beam forming unit 140 is placed co-axially with the cannula 120. However, these axes can also differ when the beam forming unit 140 is not co-axial with the cannula 120. The cannula-axis, the beam forming unit-axis and other analogous axes of the system will be commonly referred to as examples of a probe-axis.

The scanning probe 100 can also include a fiber actuator 150, housed at least partially in the handle 110. The fiber actuator 150 can be configured to move the distal fiber-portion 132 to scan the deflected beam 4 along a scanning curve 6 in the target region. In some embodiments, a substantial portion of the fiber actuator 150 can be housed in the handle 110, or even outside the handle 110. In either of these embodiments, the fiber actuator 150 can be housed separate from a disposable portion of the scanning probe 100. In some embodiments, the fiber actuator 150 can include a small portion positioned in the cannula 120, shown by the dashed actuator portion. The actuator 150 being able to scan the deflected beam 4 along a scanning curve may address the above problem (1) by providing a curved scanning functionality. The positioning of the actuator 150 may address the above outlined problem (3) by a substantial portion of the actuator 150 being positioned outside the cannula 120, away from the disposable portion of the probe 100.

In some embodiments, the fiber actuator 150 can be configured to be controlled by an actuator controller 152, positioned at least partially outside the probe 100.

In various embodiments, the scanning curve 6 can be an open curve, an arc, a closed loop, a circle, a cycloid, and an ellipse. In FIG. 1 the scanning curve 6 is a loop. In some embodiments the beam forming unit 140 can include a GRIN lens, a lens, a lens system, or a focusing element to form the deflected beam 4 by focusing the received light.

Figure 2:
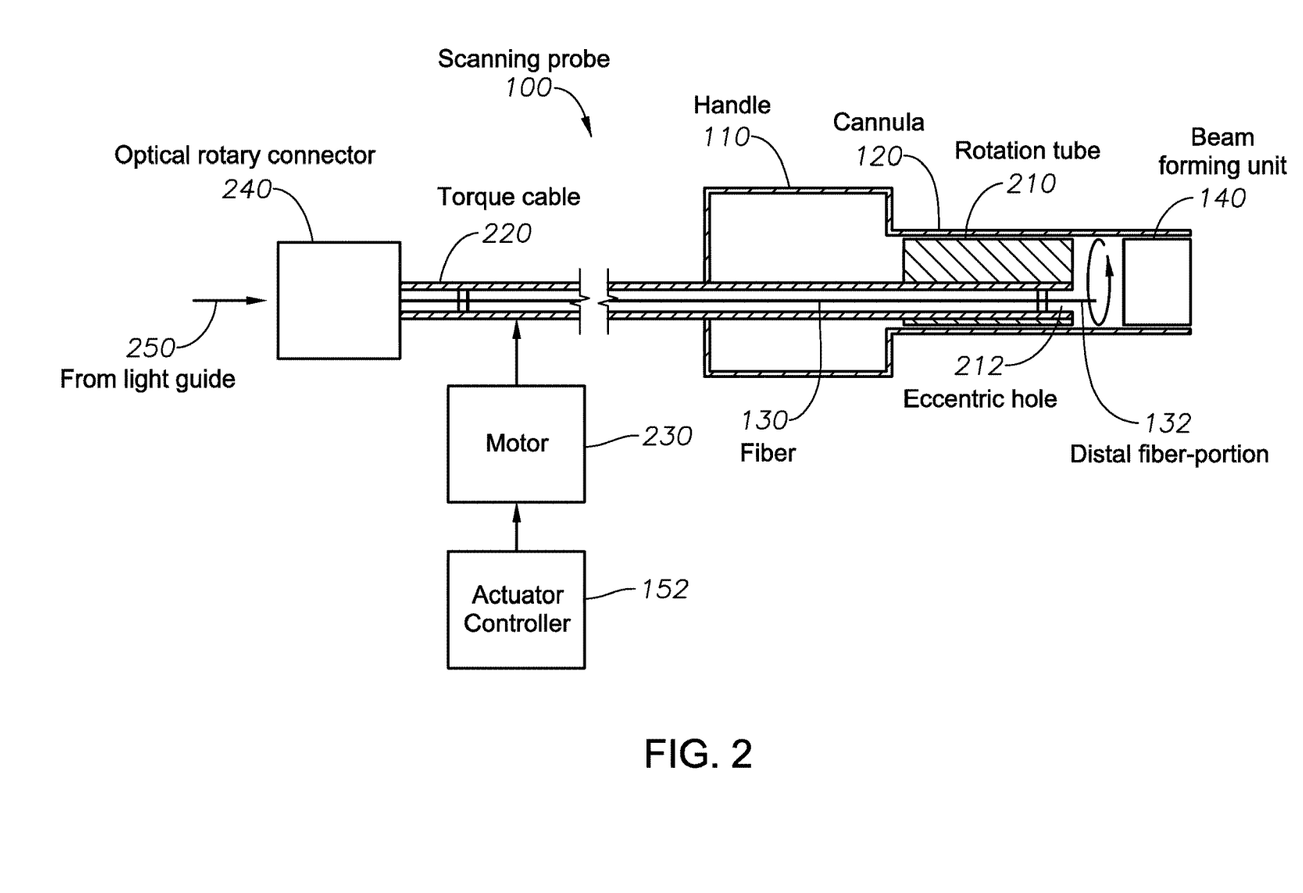
FIG. 2 illustrates an imaging probe with a torque cable.

FIG. 2 illustrates an embodiment of the probe 100 that can have several elements analogous to the embodiment of FIG. 1. In the embodiment of FIG. 2, a portion of the fiber actuator 150 can be positioned in the cannula 120: a rotation tube 210, rotatably positioned in the cannula 120 and having an eccentric hole 212 off the cannula-axis 122. Further, the fiber actuator 150 can include a hollow torque cable 220, with a distal portion inside the cannula 120, configured to be rotatable by a motor 230, and configured to rotate the rotation tube 210 when rotated by the motor 230. The hollow torque cable 220 can house a portion of the fiber 130 that extends into the cannula 120 to guide the fiber 130 to the eccentric hole 212. The fiber actuator 150 can be configured to circularly move the distal fiber-portion 132 by rotating the hollow torque cable 220 that rotates the rotation tube 210 with the eccentric hole 212 that is coupled to the distal fiber-portion 132. When the fiber actuator 150 circularly moves the distal fiber-portion 132, the light beam 2 that enters the probe 100 and is output as deflected beam 4 through the beam forming unit 140 can be scanned along a scanning curve 6, such as a scanning loop.

In some embodiments of the scanning probe 100 the fiber 130 can be rotatably housed inside the hollow torque cable 220 so that the fiber actuator 150 can rotate the hollow torque cable 220 without twisting the fiber 130. Such embodiments allow the motor 230 to rotate the torque cable 220 while avoiding the twisting of the fiber 130.

In some embodiments, the fiber 130 can be attached to the hollow torque cable 220 in a non-rotatable manner. Such embodiments can prevent the twisting of the optical fiber 130 by coupling the fiber 130 to a light guide 250 through an optical rotary connector 240. In other embodiments, the motor 230 can scan the distal fiber-portion 132 along a scanning curve 6 in a back-and-forth manner.

Concerning the design of the distal portion of the scanning probe 100, different embodiments can be realized. In some designs, the distal fiber-portion 132 can be disposed distal to a distal end of the torque cable 220. In others, proximal to the distal end of the torque cable 220. In some designs, a distal end of the torque cable 220 can be disposed distal to a distal end of the rotation tube 210, or proximal to the distal end of the rotation tube 210.

In some designs, the motor 230 can be housed outside the handle 110, or in a console, separate from the handle 110. The handle 110 can have a non-disposable portion and a disposable portion, and the motor 230 can be housed in the non-disposable portion to address the above problem (3) by positioning an expensive actuator component non-disposably. In some cases, the motor 230 can be housed in the disposable portion. Finally, in embodiments, the actuator controller 152 can control an operation of the motor 230.

Figure 3:
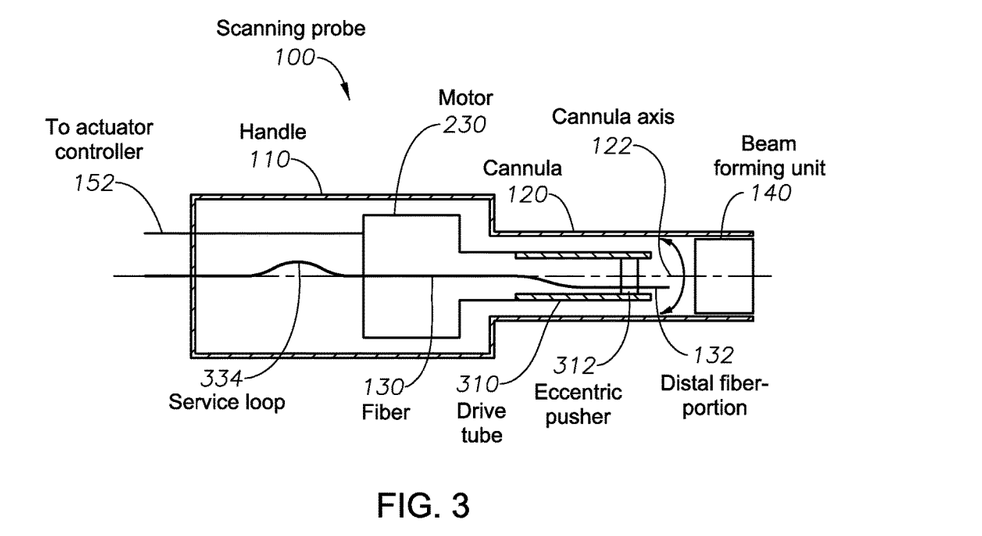
FIG. 3 illustrates an imaging probe with an eccentric pusher.

FIG. 3 illustrates an embodiment of the scanning probe 100 that again can include several elements analogous to those in FIGS. 1 and 2. In the embodiment of FIG. 3, a portion of the fiber actuator 150 can again be positioned in the cannula 120: a rotatable hollow drive tube 310, coupled to the motor 230 that can be positioned at least partially inside the handle 110. The drive tube 310 can be rotatable in the cannula 120 by the motor 230. An operation of the motor 230 can be again controlled by the actuator controller 152, coupled to the motor 230 by an electric, mechanic, electro-mechanic or pneumatic coupling. The drive tube 310 can house a portion of the fiber 130 that extends into the cannula 120. The drive tube 310 can also include an eccentric pusher 312 in a distal region of the drive tube 310 to keep the distal fiber-portion 132 off the cannula-axis 122.

In some embodiments of the scanning probe 100, the distal fiber-portion 132 can be attached to the eccentric pusher 312. In such embodiments of the probe 100, the fiber 130 gets twisted to some degree as the drive tube 310 and the eccentric pusher 312 are rotated by the motor 230. Such embodiments can include a service loop 334 in the fiber 130 to accommodate a twisting of the fiber 130 when the motor 230 rotates the drive tube 310. To limit the twisting of the fiber 130, the fiber actuator 150 can be configured to rotate the drive tube 310 and thus the distal fiber-portion 132 reciprocally, that is, back-and-forth along a scanning arc, sometimes called in a reciprocal manner. For example, the scanning arc can extend from minus 180 degree to plus 180 degree. In other embodiments, the scanning arc can extend from minus 90 degree to plus 90 degree. In yet other embodiments, the scanning arc can extend in a range between these two examples.

Figure 4:
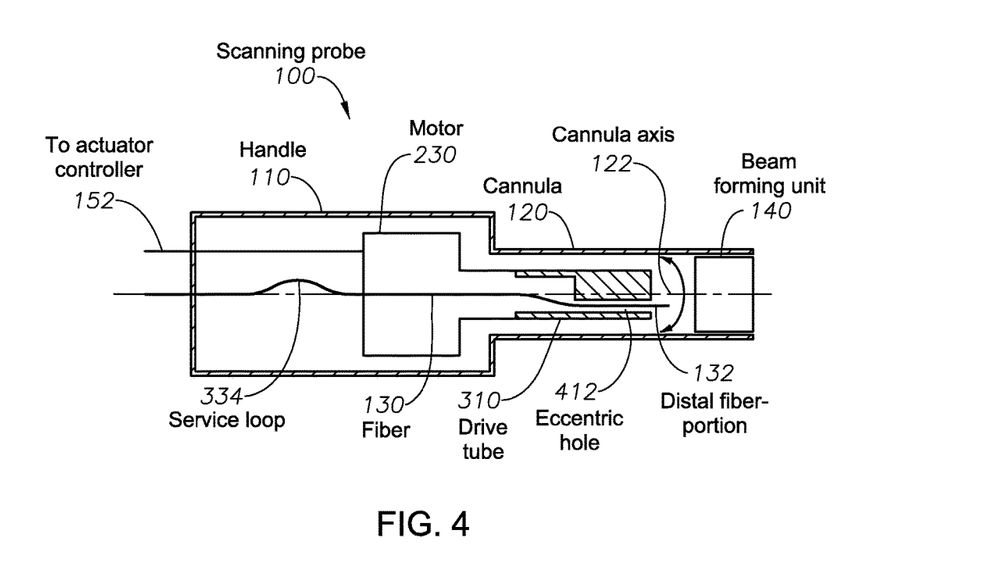
FIG. 4 illustrates an imaging probe with an eccentric hole.

FIG. 4 illustrates another embodiment of the scanning probe 100. The embodiment of FIG. 4 can include numerous elements that are analogous to those in FIGS. 1-3. In the scanning probe 100 of FIG. 4, the fiber actuator 150 can include the motor 230, positioned at least partially inside the cannula 120, the rotatable hollow drive tube 310, positioned at least partially inside the cannula 120, coupled to the motor 230 to be rotated in the cannula 120. The drive tube 310 can house a portion of the fiber 130 that extends into the cannula 120, and include an eccentric hole 412 in a distal region of the drive tube 310 to keep the distal fiber-portion 132 off the cannula-axis 122.

In contrast to the embodiment of FIG. 3, in the fiber actuator 150 of FIG. 4 the distal fiber-portion 132 can be rotatably positioned in the eccentric hole 412, so that the fiber 130 is not twisted when the motor 230 rotates the drive tube 310. Such embodiments of the scanning probe 100 can perform not only reciprocal, back-and-forth type scanning, but also circular scanning as well, as indicated.

In some embodiments, the beam forming unit 140 can include a glass element, a no-core fiber, or a glass rod. These elements can be attached to a GRIN lens. These, as well as other optical elements can shape or deflect the beam emitted from the distal fiber-portion 132.

In some embodiments, the fiber actuator may not extend into the cannula 120. Instead, in these embodiments the distal end of the fiber 130 with the distal fiber-portion 132 can be positioned proximal to the cannula 120, i.e. inside the handle 110. The beam emitted by the distal end of the fiber 130 can be forwarded to a relay lens inside the cannula 120, sometimes positioned near the fixed beam forming unit 140.

As discussed before, systems where the fiber actuator is positioned in a disposable handle can be quite costly since when the handle is disposed after a surgical procedure, it takes with it the pricey actuator as well. To reduce this cost, in embodiments of the scanning probe 100 a valuable portion of the fiber actuator 150, such as the motor 230, can be positioned in a non-disposable handle 110, or in a non-disposable portion of the handle 110. For example, in some embodiments, the entire handle 110 may be non-disposable, and only the cannula 120 can be disposed after each procedure. In other embodiments, the handle 110 can have a proximal non-disposable portion and a distal, disposable portion. In all of these embodiments, a valuable portion of the fiber actuator 150, such as the motor 230, can be in the non-disposable handle 110, or in the proximal, non-disposable portion of the handle 110.

Of course, in some probes 100 a portion of the fiber actuator 150 can be positioned in a disposable portion of the handle 110.

As mentioned before, embodiments of the optical light scanning probe 100, described in relation to FIGS. 1-4, can be used for several different functions. These include imaging, photocoagulation and ablation.

Figure 5A:
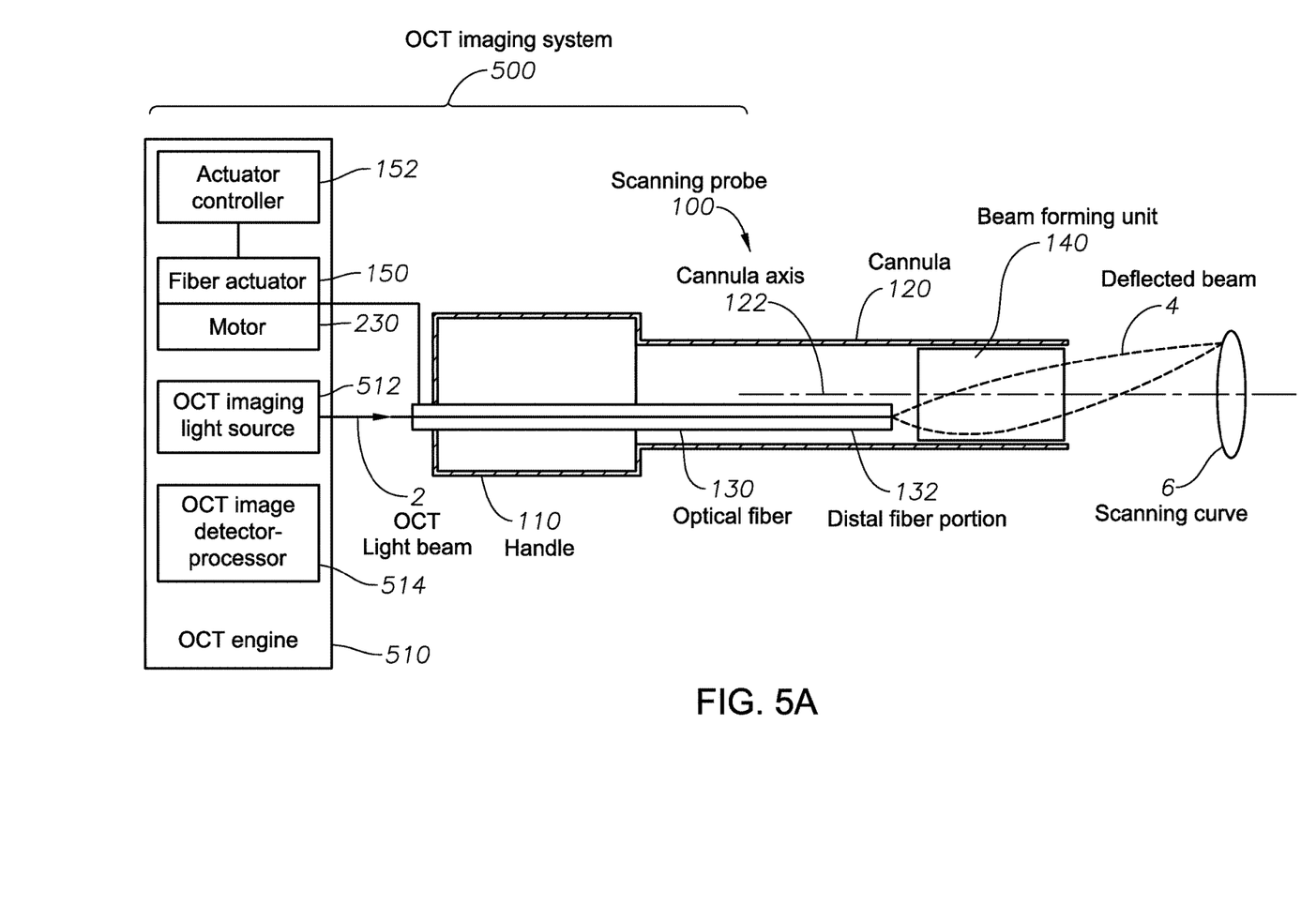
FIGS. 5A-B illustrate an OCT imaging system.
Figure 5B:
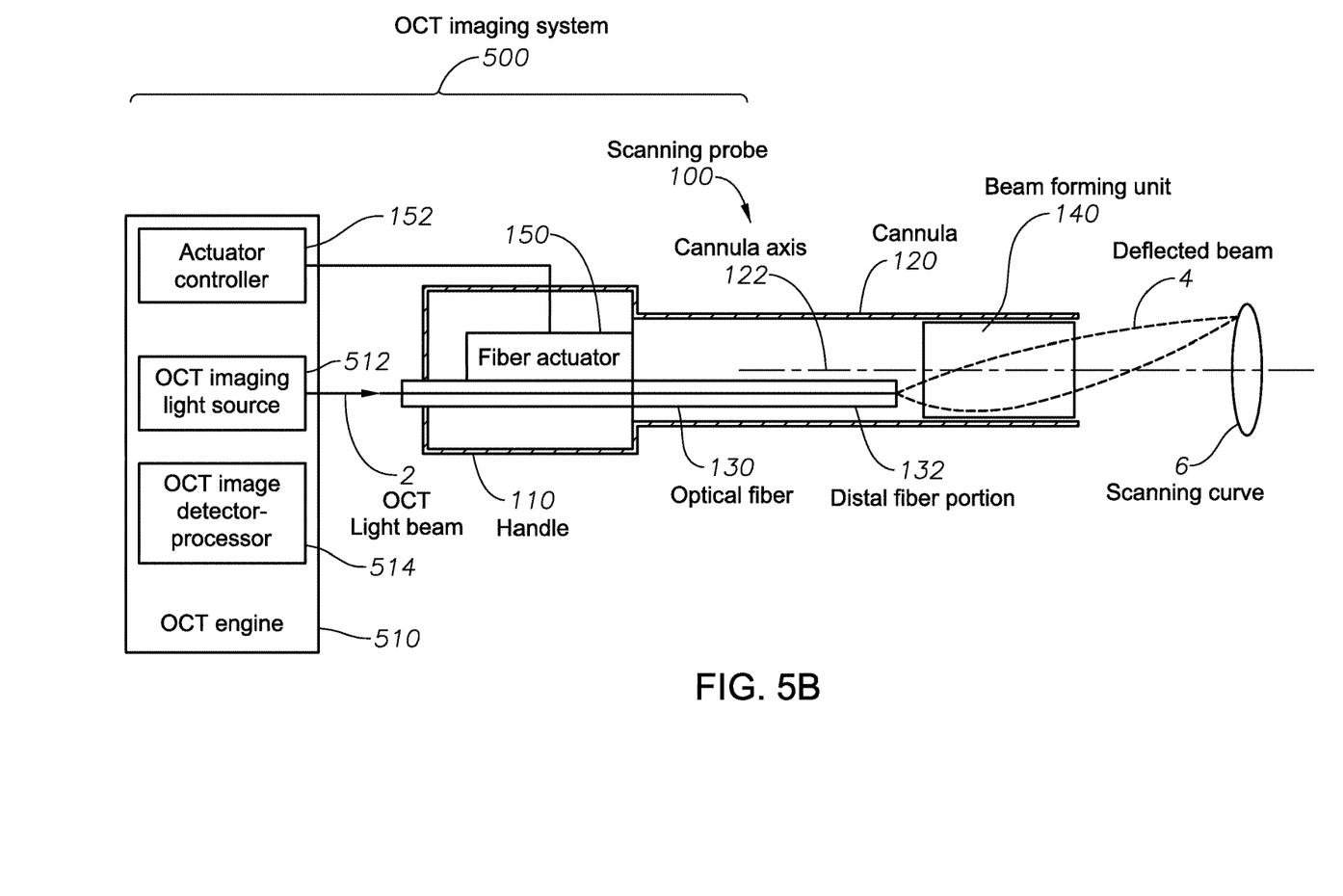

FIGS. 5A-B illustrate that embodiments of the scanning probe 100 can be part of an Optical Coherence Tomography (OCT) imaging system 500. The scanning probe 100 can be coupled, for example, to an Optical Coherence Tomography (OCT) engine 510. The OCT engine 510 can include an OCT imaging light source 512 that emits the light to the optical fiber 130. The OCT engine 510 can also be configured to detect the imaging beam, returned from the target by the scanning probe 100 and to generate an OCT image from an interference of the returned imaging beam and a reference beam by an OCT image detector-processor 514. Many OCT imaging systems are known and can all be used with the probe 100.

FIG. 5A illustrates that in some embodiments, a portion of the fiber actuator 150, such as the motor 230 that rotates the torque cable 220 of FIG. 2, can be positioned in a console of the OCT engine 510. In some embodiments, the fiber actuator controller 152 can also be part of the OCT engine 510, as shown.

FIG. 5B illustrates that in other embodiments, the actuator controller 152 can be included in the console of the OCT engine 510, while at least portions of the fiber actuator 150, such as its motor 230 can be positioned in the handle 110 as in FIGS. 3-4.

Figure 6:
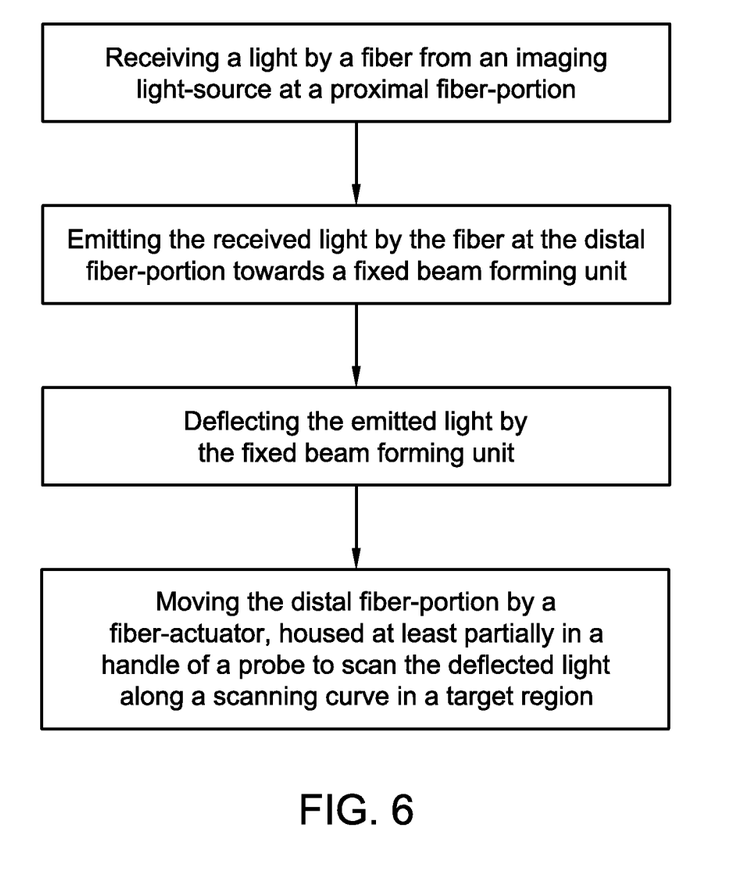
FIG. 6 illustrates a method of imaging with an imaging probe.

FIG. 6 illustrates a method 600 of operating embodiments of the scanning probe 100. The scanning probe 100 can be any of the embodiments described in relation to FIGS. 1-5. The method 600 can include:
- receiving a light (610) by a fiber from an imaging light-source at a proximal fiber-portion;
- emitting the received light (620) by the fiber at the distal fiber-portion towards a fixed beam forming unit;
- deflecting the emitted light (630) by the fixed beam forming unit; and
- moving the distal fiber-portion (640) by a fiber-actuator, housed at least partially in a handle of an imaging probe, so that the light beam deflected by the fixed beam forming unit scans along a scanning curve in a target region.

The examples provided above are exemplary only and are not intended to be limiting. One skilled in the art may readily devise other systems consistent with the disclosed embodiments which are intended to be within the scope of this disclosure. As such, the application is limited only by the following claims.

The invention claimed is:

1. An optical light scanning probe, comprising:
a handle, shaped for grasping by a user;
a cannula, protruding from a distal portion of the handle with an outer diameter smaller than 20 gauge, wherein an outermost surface of the cannula comprises an outermost surface of a portion of the scanning probe;
a rotation tube rotatably positioned within the cannula, wherein a distal end of the rotation tube comprises an eccentric hole positioned off a probe-axis, the eccentric hole having a central axis parallel to the to the probe-axis;
an optical fiber comprising a distal fiber-portion positioned within the eccentric hole such that the distal fiber-portion is off the probe-axis and parallel to the probe-axis, the optical fiber configured
to receive a light from a light-source at a proximal fiber-portion, and
to emit the received light at the distal fiber-portion;
a beam forming unit fixedly attached to the cannula and disposed at a distal portion of the cannula, the beam forming unit comprising at least one of a GRIN lens, a lens, a lens system, or a focusing element configured
to receive the light from the distal fiber-portion, and
to deflect the received light toward a target region; and
a fiber actuator, housed at least partially in the handle, configured to rotate the rotation tube within the cannula such that the distal fiber-portion positioned within the eccentric hole rotates around the probe-axis relative to the beam forming unit to scan the deflected light along a scanning curve in the target region, wherein
the probe-axis is one of a cannula-axis and a beam forming unit-axis.

2. The optical light scanning probe of claim 1, the scanning curve comprising one of:
an open curve, an arc, a closed loop, a circle, a cycloid, and an ellipse.

3. The optical light scanning probe of claim 1, wherein:
the fiber actuator is configured to be controlled by an actuator controller, positioned at least partially outside the probe.

4. The optical light scanning probe of claim 1, the fiber actuator comprising: a motor, configured to rotate a hollow torque cable that has a distal portion inside the cannula, wherein the hollow torque cable is configured
to rotate the rotation tube when rotated by the motor,
to house a portion of the optical fiber that extends into the cannula to guide the optical fiber to the eccentric hole.

5. The optical light scanning probe of claim 4, wherein:
the hollow torque cable houses the optical fiber rotatably so that the motor of the fiber actuator can rotate the torque cable without twisting the optical fiber.

6. The optical light scanning probe of claim 5, wherein:
the hollow torque cable houses the optical fiber in a non-rotatable manner.

7. The optical light scanning probe of claim 6, wherein:
the optical fiber is coupled to a light guide through an optical rotary connector.

8. The optical light scanning probe of claim 5, wherein:
the distal fiber-portion is disposed one of
distal to a distal end of the hollow torque cable, and
proximal to the distal end of the hollow torque cable.

9. The optical light scanning probe of claim 5, wherein:
a distal end of the hollow torque cable is disposed one of
distal to a distal end of the rotation tube, and
proximal to the distal end of the rotation tube.

10. The optical light scanning probe of claim 5, wherein:
the motor is housed outside the handle.

11. The optical light scanning probe of claim 1, wherein:
the beam forming unit comprises the GRIN lens coupled to at least one of a glass element, a no-core fiber, and a glass rod.

12. The optical light scanning probe of claim 1, wherein:
the beam forming unit comprises a relay lens.

13. The optical light scanning probe of claim 1, wherein:
a portion of the fiber actuator is positioned in a non-disposable portion of the handle.

14. The optical light scanning probe of claim 1, wherein:
a portion of the fiber actuator is positioned in a disposable portion of the handle.

15. The optical light scanning probe of claim 1, wherein:
a portion of the fiber actuator is positioned in a console, comprising an Optical Coherence Tomography imaging engine.

16. The optical light scanning probe of claim 1, wherein:
the scanning probe is part of at least one of a laser coagulation system and a laser ablation system.

17. An optical imaging system, comprising:
an Optical Coherence Tomography engine, comprising
an imaging light source, and
an OCT image detector-processor; and
an imaging probe, comprising
a handle, and
a cannula, protruding from a distal portion of the handle with an outer diameter smaller than 20 gauge, wherein an outermost surface of the cannula comprises an outermost surface of a portion of the scanning probe;
a rotation tube rotatably positioned within the cannula, wherein a distal end of the rotation tube comprises an eccentric hole positioned off a probe-axis, the eccentric hole having a central axis parallel to the probe-axis;
an optical fiber comprising a distal fiber-portion positioned within the eccentric hole such that the distal fiber-portion is off the probe-axis and parallel to the probe axis, the distal fiber-portion configured to guide a light from the imaging light-source;
a beam forming unit fixedly attached to the cannula and disposed at a distal portion of the cannula, the beam forming unit comprises at least one of a GRIN lens, a lens, a lens system and a focusing element to form a beam by focusing the received light, or a focusing element configured to deflect the guided light toward a target; and
a fiber actuator, housed at least partially in the handle, configured to rotate the rotation tube within the cannula such that the distal fiber-portion positioned within the eccentric hole rotates around the probe-axis relative to the beam forming unit to scan the deflected light along a scanning curve in a target region, wherein
the probe-axis is one of a cannula-axis and a beam forming unit-axis.

18. A method of imaging with an imaging probe that comprises a handle; a cannula, protruding from the handle with an outer diameter smaller than 20 gauge, wherein an outermost surface of the cannula comprises an outermost surface of a portion of the scanning probe; a rotation tube rotatably positioned within the cannula, wherein a distal end of the rotation tube comprises an eccentric hole positioned off a probe-axis and perpendicular to the probe-axis; an optical fiber comprising a distal fiber-portion positioned within the eccentric hole such that the distal fiber-portion is off the probe-axis, the eccentric hole having a central axis parallel to the probe-axis; and a beam forming unit fixedly attached to the cannula at a distal portion of the cannula; the method comprising:

receiving a light by the optical fiber from an imaging light-source at a proximal fiber-portion;

emitting the received light by the optical fiber at the distal fiber-portion towards the beam forming unit fixedly attached to the cannula;

deflecting the emitted light by the beam forming unit; and rotating the rotation tube within the cannula such that the distal fiber-portion positioned within the eccentric hole rotates around the probe axis relative to the beam forming unit by a fiber-actuator, housed at least partially in the handle of the imaging probe to scan the deflected light along a scanning curve in a target region, wherein    the probe-axis is one of a cannula-axis and a beam forming unit-axis.

\* \* \* \* \*